United States Patent [19]
Pusey

[11] Patent Number: 5,919,446
[45] Date of Patent: Jul. 6, 1999

[54] **CONTROL OF FIRE BLIGHT ON POME FRUIT TREES WITH *ERWINIA HERBICOLA***

[75] Inventor: P. Lawrence Pusey, East Wenatchee, Wash.

[73] Assignee: The United States of America as represented by The Secretary of Agriculture, Washington, D.C.

[21] Appl. No.: 08/958,475

[22] Filed: Oct. 27, 1997

[51] Int. Cl.⁶ .............................. A01N 63/00; C12N 1/20

[52] U.S. Cl. ..................... 424/93.4; 435/252.1; 435/847

[58] Field of Search ..................... 424/93.4; 435/252.1

[56] References Cited

U.S. PATENT DOCUMENTS 4,569,841  2/1986  Liu ............................................ 424/93

*Primary Examiner*—Irene Marx
*Assistant Examiner*—Vera Afremova
*Attorney, Agent, or Firm*—M. Howard Silverstein; John D. Fado; Margaret A. Connor

[57] ABSTRACT

A biologically pure culture of *Erwinia herbicola* NRRLB-21856 is described which is highly effective as a biological control agent against *Erwinia amylovora,* the cause of fire blight, the destructive disease of apples and pears. The invention also encompasses methods of biologically controlling fire blight disease using the bacterium of the invention, and agricultural compositions which incorporate the strain.

5 Claims, 2 Drawing Sheets

CONTROL OF FIRE BLIGHT ON POME FRUIT TREES WITH ERWINIA HERBICOLA

BACKGROUND OF THE INVENTION

1. Field of the Invention

The present invention relates to a microorganism useful in the control of fire blight, a disease that damages pome fruit trees. More particularly, the invention relates to a bacterium identified as a strain of *Erwinia herbicola;* methods of using the strain to control fire blight; and agricultural compositions which incorporate the bacterium, which are useful in such methods.

2. Description of the Art

Fire blight disease, caused by the bacterium *Erwinia amylovora,* can be a devastating disease of pome fruit trees (Malus, Pyrus), and is a major constraint to pome fruit production in many areas of the world. Fire blight is most commonly initiated by epiphytic populations of *Erwinia amylovora* that develop on blossoms. Under relatively dry climatic conditions, it is thought that bacterial colonization occurs predominantly on flower stigmas, and subsequent rain or heavy dew facilitates movement to the hypanthia where infection generally occurs. Infected blossoms first appear water soaked; then they wilt, shrivel, and turn brown to black. Progression of the infection leads to similar symptoms on other parts of the tree. The most obvious symptom on pear or apple trees is the scorched appearance of leaves on affected branches. Although in the Pacific Northwest, fire blight outbreaks are episodic and only occasionally serious, in temperate climates with high seasonal precipitation, the disease can be production limiting. Pears are no longer commercially produced on the East coast because of this disease.

Considerable expense is incurred by the tree fruit industry each year for labor and chemical costs for fire blight management, as well as to meet stringent export protocols required by some importing countries to minimize the likelihood of pathogen spread. Current control measures rely on a combination of predictive modeling of infection periods, antibiotic spray application, and cultural controls (pruning and sanitation). While control programs have focused on the suppression of *Erwinia amylovora* on floral parts through the use of antibiotics, the usefulness of this approach has decreased because pathogen resistance to streptomycin has developed in many production areas, and the less effective antibiotic oxytetracycline has been substituted.

Microbial biocontrol of the blossom blight phase of fire blight has been proposed as an alternative to antibiotics (Beer et al., *Acta Horticulturae* 151:195–201 (1984); Epton et al., In: *Ecology of Plant Pathogens,* (Eds.) J. P. Blakeman and B. Williamson, pages 335–352, CAB International, Wallingford (1994); Johnson et al., *Phytopathology* 83:478–484 and 995–1002 (1993); Vanneste et al., *Acta Horticulturae* 273:409–410 (1990) and 411:351–353 (1996); and Wilson et al., *Phytopathology* 83:117–123 (1993)); or as a measure that could complement the use of antibiotics (Lindow et al., *Phytopathology* 86:841–848 (1996) and Stockwell et al., *Phytopathology* 86:834–840 (1996)). The strains most often referred to in published studies on biological control of fire blight include *Pseudomonas fluorescens* strain A506, *Erwinia herbicola* strain C9-1, and *Erwinia herbicola* strain Eh252. U.S. Pat. No. 4,569,841 to Liu reports *Erwinia herbicola* strain EHO-10 as having broad spectrum inhibitory activity against pathogenic bacteria including *Erwinia amylovora,* in in vitro studies. Recently, the product Blightban® (active ingredient, *Pseudomonas fluorescens* strain A506) produced by Plant Health Technologies (Boise, Id.) became available commercially.

SUMMARY OF THE INVENTION

The present invention is directed to a biologically pure culture of a bacterium identified as a strain of *Erwinia herbicola,* which strain is highly effective as a biological control agent against fire blight, the destructive apple and pear disease caused by *Erwinia amylovora.* The subject bacterium is identified as *Erwinia herbicola* strain E325.

A further aspect of the present invention are methods of biologically controlling fire blight using the bacterium of the invention. This aspect includes use of this bacterium to inhibit the incidence or severity of the disease caused by the pathogen *Erwinia amylovora* on pome fruit trees, particularly on the blossoms.

A still further aspect of the invention pertains to agricultural compositions which incorporate the strain of the invention, and which may be utilized in carrying out the aforementioned methods. Such compositions include the microorganism in combination with an agricultural carrier.

In accordance with this discovery, it is an object of the invention to provide a unique strain of *Erwinia herbicola* which provides biocontrol of fire blight on pome fruit which is greater than known biocontrol strains.

It is also an object of the invention to provide a biologically pure culture of *Erwinia herbicola* which is highly effective as a biological control agent against *Erwinia amylovora,* the cause of fire blight.

Another object of the invention is the provision of methods for biologically controlling fire blight on pome fruit using the strain of the invention and agricultural compositions which incorporate the strain.

Other objects and advantages of the invention will become readily apparent from the ensuing description.

DETAILED DESCRIPTION OF THE INVENTION

Figure 1:
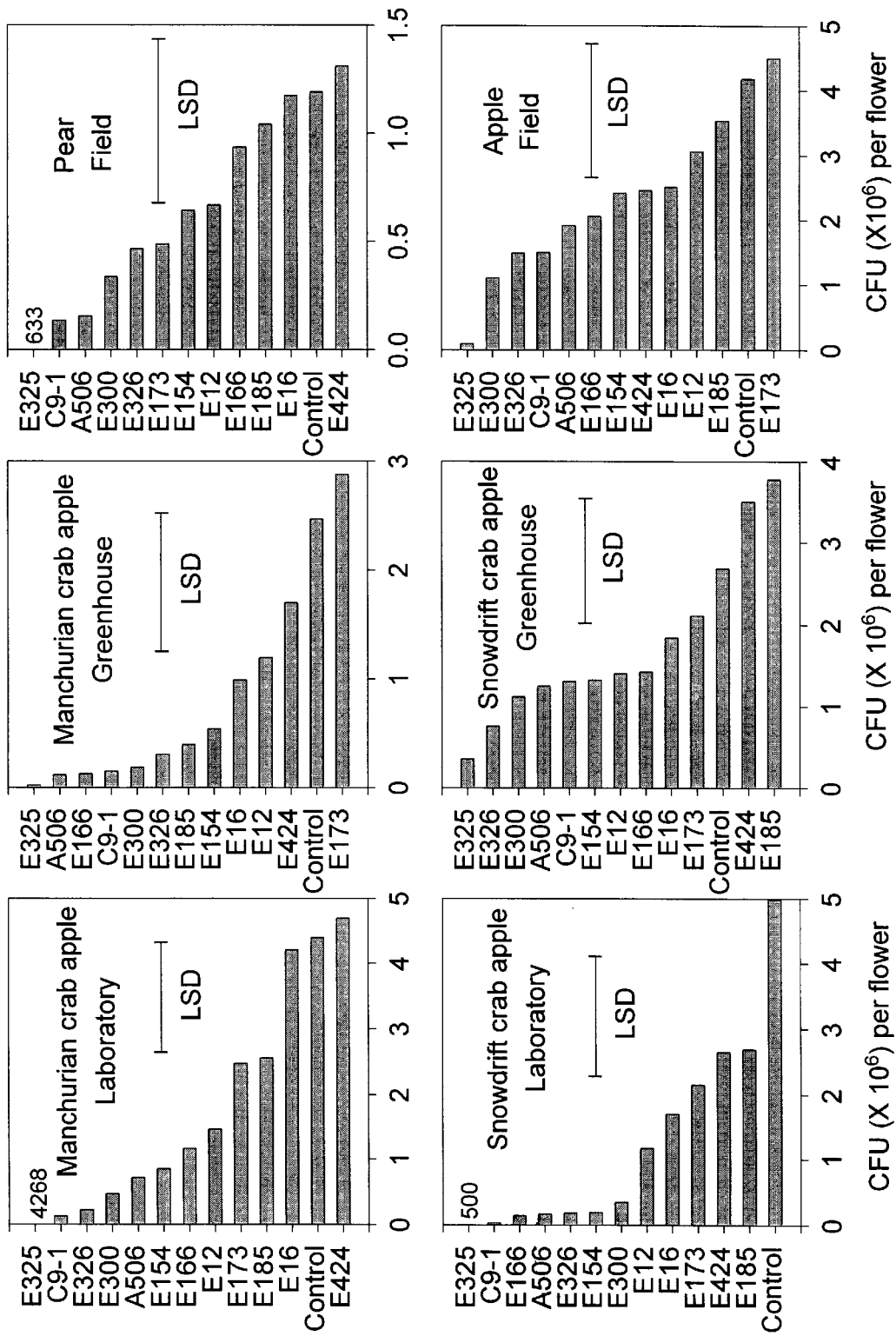
FIG. 1 shows the effects of selected bacterial strains, including the strain of the invention, on stigmatic populations of *Erwinia amylovora* in tests conducted with crab apple blossoms ('Manchurian' and 'Snowdrift') in the laboratory and greenhouse and with apple and pear blossoms in the field. Each bar represents the mean population size of *Erwinia amylovora* per flower treated with a test strain indicated by code on the Y axis. Ten flowers were used per strain per each of two tests, and data from the two tests were pooled. Test strains, from top to bottom, are in order of greatest to least effective in reducing populations of *Erwinia amylovora.* Line indicates least significant difference (LSD) at $P \leq 0.05$.

The unique bacterial strain of the invention was isolated in the spring of 1994 from apple blossoms on a tree located about 10 miles north of Wenatchee, Wash. It was obtained in biologically pure form by dilution plating and was designated *Erwinia herbicola* E325. It was selected from over 600 other bacteria and yeasts that were tested on detached blossoms of crab apple in the laboratory. The origin and isolation of E325 are described in detail, below, in Example 1.

The strain of the invention is highly effective as a biological control agent against fire blight, as shown by assays with detached crab apple blossoms which assess the ability of a microorganism to suppress the pathogen *Erwinia amylovora* on flowers, and which have proved to be a reliable predictor of field performance of biocontrol agents on apple and pear blossoms, where fire blight infections are generally initiated. Additionally, field trials indicate that strain E325 is more effective than other biocontrol agents in suppressing the pathogen and controlling fire blight.

The E325 strain has been shown in numerous laboratory experiments to be significantly more effective than all other strains tested in reducing *Erwinia amylovora* populations of flower stigmas and in reducing disease incidence. On the average, *Erwinia amylovora* populations on flowers are reduced by E325 to levels approximately 100-fold lower than those on flowers treated with *Pseudomonas fluorescens* strain A506, the active ingredient in Blightban®, the only commercial biological control product available for fire blight. The difference compared with *Erwinia herbicola* strains Eh252 and C9-1 (strains of *Erwinia herbicola* most often referred to in published studies on biological control of fire blight) was about 10 to 100-fold. Strain E325 was also repeatedly superior to other selected bacteria, including strains A506 and C9-1, in suppressing floral populations of *Erwinia amylovora* in field tests with apple and pear. Studies showing the effectiveness of strain E325 compared to other microorganisms are described in detail, below, in Examples 3 and 4.

The identifying taxonomic characteristics of *Erwinia herbicola* E325 are as follows: The E325 strain morphologically is a short rod, is gram negative, and produces yellow pigment when cultured on conventional bacteriological media, such as nutrient agar or King's B. It was identified as the bacterium *Pantoea agglomerans* (Beijerinck) Gavini et al. [synonym: *Erwinia herbicola* (Geilinger) Dye] based on fatty acid methyl ester analysis of whole cell fatty acids using gas chromatography and profile analysis with the Microbial Identification System software (Microbial ID, Inc., Newark, Del.) which gave a similarity index of 0.805. This was confirmed based on carbon utilization analysis with the Biolog system (Biolog, Inc., Hayward, Calif.) which gave a similarity index of 0.759.

Carbon utilization test results according to the Biolog system are indicated in parentheses for each carbon source as follows: α-cyclodextrin (−), dextrin (+), glycogen (+), tween 40 (+), tween 80 (+), N-acetyl-D-galactosamine (−), N-acetyl-D-glucosamine (+), adonitol (−), L-arabinose (+), D-arabitol (−), cellobiose (−), I-erythritol (−), D-fructose (+), L-fructose (−), D-galactose (+), gentiobiose (+), α-D-glucose m-inositol (+), α-D-lactose (−), lactulose (−), maltose (+), D-mannitol (+), D-mannose (+), D-melibiose (−), β-methyl D-glucoside (+), D-psicose (+), D-raffinose (−), L-rhamnose (+), D-sorbitol (+), sucrose (+), D-trehalose (+), turanose (−), xylitol (−), methyl pyruvate (+), mono-methyl succinate (+), acetic acid (+), cis-aconitic acid (+), citric acid (−), formic acid (−), D-galactonic acid lactone (−), D-galacturonic acid (+), D-gluconic acid (+), D-glucosaminic acid (−), D-glucuronic acid (+), α-hydroxybutyric acid (−), β-hydroxybutyric acid (−),γ-hydroxybutyric acid (−), p-hydroxy phenylacetic acid (−), itaconic acid (−), α-keto butyric acid (−), α-keto glutaric acid (−), α-keto valeric acid (−), D, L-lactic acid (+), malonic acid (+), propionic acid (−), quinic acid (+), saccharic acid (+), sebacic acid (−), succinic acid (+), bromo succinic acid (+), succinamic acid (−), glucuronamide (+), alaninamide (−), D-alanine (+), L-alanine (+), L-alanyl-glycine (+), L-asparagine (+), L-aspartic acid (+), L-glutamic acid (+), glycyl-L-aspartic acid (+), glycyl-L-glutamic acid (+), L-histidine (+), hydroxy L-proline (−), L-leucine (−), L-ornithine (−), L-phenylalanine (−), L-proline (+), L-pyroglutamic acid (−), D-serine (−), L-serine (+), L-threonine (−), D,L-carnitine (−), γ-amino butyric acid (−), urocanic acid (+), inosine (+), uridine (+), thymidine (+), phenyl ethylamine (−), putrescine (−), 2-amino ethanol (−), 2,3-butanediol (−), glycerol (+), D,L-α-glycerol phosphate (+), glucose-1-phosphate (+), and glucose-6-phosphate (+).

Statement of Deposit. a biologically pure culture of *Erwinia herbicola* E325 was deposited Oct. 24, 1997 under terms of the Budapest Treaty in the Agricultural Research Culture Collection (NRRL), 1815 North University Street, Peoria, Ill. 61604, and has been assigned the accession number NRRL B-21856. Strains having all the identifying characteristics of NRRL B-21856 are encompassed by this invention. For the purpose of this invention, any isolate having the identifying characteristics of strain E325, including subcultures and variants thereof which retain the ability to inhibit growth of *Erwinia amylovora* pathogens on pome fruit blossoms, are included. The term variants is defined herein to include transformants and mutants which are capable of inhibiting growth of *Erwinia amylovora* on pome fruit blossoms.

Growth of the strain of the invention. *Erwinia herbicola* E325 can be grown on any suitable solid or liquid bacteriological medium. For routine production of strain E325 for treatment of flowers in the laboratory or field, the bacterium is grown on nutrient-yeast-dextrose agar (NYDA; nutrient broth, 8 g: yeast, 5 g; dextrose, 5 g; agar, 15 g; and deionized water, 1 L) for 24 hours at 24° C. Bacterial growth is scraped from the agar surface with a microbiological loop or rubber spatula and suspended in 10 mM potassium phosphate buffer (pH 7.0) and 0.03% Tween-20. Cell concentration is adjusted using spectrophotometry; an absorbance of 0.1 at 600 nm wavelength indicates a concentration of approximately $10^8$ CFU/ml. Strain E325 is conveniently stored on silica gel at −20° C. To do this, it is transferred with a loop from a 24-hour culture on NYDA to 4% milk. Conveniently, a 100-μl aliquot of the suspension is pipetted onto 1.5 g of silica gel in a 6-ml vial. New cultures are periodically started by sprinkling silica gel onto agar media.

Use of the strain of the invention. *Erwinia herbicola* E325 is useful in the control of fire blight on pome fruit trees. The term pome fruit applies to plants in the family Rosaceae that produce a fleshy fruit having seeds but no stone, such as apple, pear and quince. For purposes of the invention, control means that flower populations of *Erwinia amylovora,* the bacterium that causes fire blight, are reduced compared to untreated trees. Consequently, the incidence or severity of fire blight is reduced or prevented. The affect of control treatments on disease will be evidenced by the lower number of blackened flowers and flower clusters and by a lower number of blighted shoots on trees.

The strain is preferably incorporated into compositions suitable for application to pome fruit trees, preferably for blossom application. It can be mixed with any agriculturally acceptable carrier or suitable agronomically acceptable carrier which does not interfere with the activity of the strain, for example, water or buffer. Where the strain is applied as a suspension or emulsion in a liquid carrier, the suspension or emulsion may optionally contain conventional additives such as surfactants, wetting agents or chemical inhibitors as known in the art. The strain of the invention can also be formulated to include other fire blight biocontrol strains.

The organism of the invention is applied to pome fruit trees, and particularly the blossoms, using conventional methods such as spraying. Application is made during flower bloom, since the flower (blossom) is the primary infection site. Generally, application is made once during early bloom (10–20% of flowers opened) or twice, at early bloom (10–20%) and then again later during bloom (90–100%).

The strain is applied in an effective amount. For the purposes of this invention, an effective amount is defined as that quantity of microorganism cells sufficient to inhibit the incidence or development of *Erwinia amylovora* when applied to pome fruit blossoms. Typically, a concentration range from about $5\times10^6$ to $1\times10^9$ colony forming units (CFU)/ml is effective. The preferred concentration range is about $1\times10^7$ to $1\times10^8$ CFU/ml; however, concentrations as low as $1\times10^6$ CFU/ml may be useful in some cases. The effective rate can be affected by environmental factors which can affect both the biocontrol agent and the pathogen. Whether or not an orchard has had a history of fire blight also relates to pathogen inoculum levels and effective rates of the biocontrol agent. The amount that will be within an effective range in a particular instance can be determined by laboratory assays and disease prediction models based on temperature and precipitation.

EXAMPLES

The following examples are intended only to further illustrate the invention and are not intended to limit the scope of the invention which is defined by the claims.

Example 1

The following example describes the origin and isolation of *Erwinia herbicola* E325.

The E325 strain was originally isolated from blossoms of Gala apple trees at Columbia View, about 10 miles north of Wenatchee, Wash., in mid-April 1994. It was discovered during a two-year study of the natural microflora on the surfaces of apple blossoms in the Pacific Northwest. Each flower was removed with sterile forceps from the tree and later aseptically dissected to remove sepals, petals and anthers. Stigmas along with supporting styles were then placed in one microcentrifuge tube and the floral cup at the base of the pistil (hypanthium) was placed in another microcentrifuge tube. Each of the microcentrifuge tubes, which contained 0.99 ml of sterile buffer (10 mM potassium phosphate, pH 7.0), were vortexed for 2 to 3 seconds and placed in a sonication bath (Braun, Model 3200, Bronson Cleaning Equipment Co., Shelton, Conn.) for 60 seconds. The samples were again vortexed for 2 to 3 seconds and two one-hundred-fold serial dilutions were prepared in phosphate buffer. A 10-$\mu$l sample of each dilution was plated on TSA (tryptone, 15 g; soytone, 5 g; NaCl, 5 g; agar, 15 g; and deionized water, 1 liter) amended with streptomycin sulfate (50 $\mu$g/ml) and on TSA amended with cycloheximide (50 $\mu$g/ml). The E325 strain was taken from a single colony that showed up on the latter medium, to which had been plated the buffer wash and serial dilutions from hypanthium tissue. Stock cultures were maintained as described above.

Example 2

This example describes the selection of strain E325 from among other microorganisms.

Materials and Methods.

The E325 strain was selected from more than 600 other bacteria and yeasts that have so far been tested in the laboratory for potential use in the biological control of fire blight. The screening method used was developed by the inventor and involves detached blossoms of crab apple. Results of this technique were shown to correlate with field trials involving apple and pear trees.

Crab apple trees were selected as a model for the study and detection of fire blight biocontrol agents because of their high flower productivity on current season growth (apple and pear wood generally must be 2-years-old before flowering), high susceptibility to fire blight, and availability from nurseries (as they are widely propagated and sold as pollinators for apple). 'Manchurian' and 'Snowdrift' crab apple trees (16 mm minimum diam. on M.9 or M.26 rootstock) were obtained from nurseries in Washington State. From January until June or July of each year, dormant trees were weekly transferred by groups from a cold room (1 to 2° C.) to a greenhouse where they were forced to bloom. The period that trees were held in the cold room after being received from the nursery ranged from zero to 5 months. After a growth period of about 5 months, but no cold dormancy, trees were induced to flower a second time. For each tree, leaves were manually removed and a solution of 1% cytokinin [N-(phenylmethyl)-1H-purine 6-amine] and 0.1% gibberellins $A_4A_7$ (active ingredients in Accel, Abbott Laboratories, North Chicago, Ill.) was brushed once onto the buds. On a weekly basis, tree groups were treated in the same order as above, from June or July until the following January or February. Bloom occurred 2 to 3 weeks after the transfer of trees from the cold room (first bloom) or the application of growth regulators (second bloom). The above procedures resulted in the continual availability of flowers for year-around studies in the laboratory and greenhouse.

To screen microorganisms, newly opened flowers were collected from trees in the greenhouse. Each detached flower was maintained with the cut peduncle submerged in 25% sucrose solution in a single vial, and vials were supported in plastic tube racks. Bacteria were cultured on nutrient-yeast-dextrose agar (nutrient broth, 8 g; yeast, 5 g; dextrose, 5 g; agar, 15 g; and deionized water, 1 L) for 24 h at 24° C. and cell suspensions were prepared in 10 mM potassium phosphate buffer (pH 7.0) and 0.03% Tween-20. Test strains were suspended at $10^8$ CFU/ml and applied to flowers by touching a droplet of the suspension to each stigma to form a thin film of moisture (0.1 to 0.2 $\mu$l per flower). Flowers were allowed to air dry in a laminar flow hood, and then were enclosed in 4-L plastic containers (Rubbermaid®, Twinsburg, Ohio) and incubated at 24° C. No water, other than that in the sucrose solution in vials, was added to the containers. Relative humidity was measured at 60 to 65% using a hand-held meter with a probe that was inserted through a small hole in each container. After 24 hours, a nalidixic acid-resistant derivative of *Erwinia amylovora* strain Ea153 (obtained from K. Johnson, Oregon State University, Corvallis) was suspended at $10^7$ CFU/ml and similarly applied to the flowers. After another 24 hours, population size of Ea153 on flower stigmas was determined by placing stigmas and supporting styles of each flower in sterile microcentrifuge tubes containing 1 ml of sterile buffer (10 mM potassium phosphate, pH 7.0). Tubes were vortexed for 2 to 3 sec, sonicated for 60 seconds, vortexed again for 2 to 3 seconds, and then serial dilutions were prepared and plated on CCT medium (Ishimaru and Klos, *Phytopathology* 74:1342–1345 (1984)) (sucrose, 100 g; sorbitol, 10 g; 1% aqueous solution of tergitol anionic 7, 30 ml; 0.1% crystal violet in absolute ethanol, 2 ml; nutrient agar, 23 g; and deionized water, 970 ml) amended with nalidixic acid (50 µg/ml)). After 3 to 4 days of incubation at 24° C., bacterial colonies were counted.

Among the more than 600 bacteria tested as described above, strain E325 was the most effective in suppressing populations of *Erwinia amylovora* on flower stigmas.

Example 3

This example describes a series of tests in which *Erwinia herbicola* strain E325 was compared to selected bacterial strains representing several different species. In addition to laboratory assays with detached blossoms as above, tests were also performed with blossoms of crab apple in the greenhouse and blossoms of pear and apple in the field.

Materials and Methods.

Bacterial strains. Bacteria obtained from other workers were a nalidixic-acid-resistant derivative of *Erwinia amylovora* strain Ea153, rifampicin-resistant *P. fluorescens* strain A506, and a rifampicin-resistant derivative of *Erwinia herbicola* strain C9-1. Original strain codes, without letters previously added to indicate specific derivative types, are used in this report. The pathogen or control strain, Ea153, was obtained from K. Johnson, Oregon State University, Corvallis, who isolated it from cankers on Gala apple in Oregon. Strain A506, originally from Steve Lindow, University of California, Berkeley, was isolated from pear in California and reduced fire blight incidence. Strain C9-1, originally from C. Ishimaru, Colorado State University, Fort Collins, was isolated from Jonathan apple fruit in Michigan and produced at least two antibiotics, herbicolins O and I, that are inhibitory to *Erwinia amylovora*. The rifampicin-resistant derivative of C9-1 mixed with A506 reduced fire blight of pear.

Ten other bacteria used were isolated from apple blossoms near Wenatchee in 1994, and together these represented a range of biocontrol activities based upon preliminary laboratory assays with detached crab apple blossoms. Rifampicin-resistant derivatives were generated spontaneously from each of the 10 strains for use in this study. Identifications were made based on fatty acid methyl ester analysis of whole-cell fatty acids using gas chromatography and profile analysis with Microbial Identification System software (Microbial, ID, Inc., Newark, Del.). The bacteria were identified as *Arthrobacter protophormiae* (E424), *Bacillus pumilus* (E185), *Curtobacterium flaccumfaciens* (E16), *Erwinia herbicola* (E325) (the strain of the invention), *Pseudomonas chloroaphis* (E326), *Pseudomonas cichorii* (E173), *P. fluorescens* (E166), *Pseudomonas marginalis* (E154), *Pseudomonas putida* (E300), and *Pseudomonas syringae* (E12).

All twelve bacterial strains listed above were tested against the control strain Ea153 on detached blossoms of Manchurian and Snowdrift crab apple in the laboratory, on blossoms of intact trees of both crab apple cultivars in the greenhouse, and on blossoms of 'Bartlett' pear and 'Gala' apple trees in the field. Procedures were the same as those described above for detached blossoms in the laboratory, with the following exceptions. In the greenhouse and field, unopened flowers in the "popcorn" stage of development were tagged on one day and treated with test bacteria on the following day when the flowers were open. Suspensions of the test bacteria ($10^8$ CFU/ml) and the pathogen ($10^7$ CFU/ml) were applied with a pipette by dispensing 0.5 µl of suspension to the stigma. Detached blossoms were allowed to dry in a laminar flow hood as before, but no effort was made to accelerate drying in the greenhouse or field. In the greenhouse, where the average daily maximum and minimum temperature was 30.0 and 20.5° C., inoculations and determination of bacterial populations were done according to the same schedule given for laboratory assays. In the field, however, temperatures were lower (the daily maximum ranged from 12.2 to 22.3° C. and the daily minimum ranged from −1.4 to 8.2° C.), and so more time was allowed for bacterial colonization. The time interval between application of the test bacteria and the pathogen was 48 hours for pear and 24 hours for apple; the time interval between inoculation with the pathogen and collection of flowers for population determination was 48 hours for both pear and apple. Greenhouse and field samples were processed immediately after collection to determine microbial population sizes on the stigmas. Populations of *Erwinia amylovora* were determined as described above and those of the test bacteria were determined on Kings medium B amended with rifampicin (25 µg/ml) and cycloheximide (50 µg/ml).

Results.

In all of the above tests, which included field trials with both pear and apple trees, population sizes of *Erwinia amylovora* on flowers treated with strain E325 were 10–100 fold lower than those on flowers treated with any other bacterium (FIG. 1). When data was transformed to log numbers, the difference was always statistically significant ($P \leq 0.05$).

In the field test with pear, pathogen suppression by strain E325 was more than 100-fold greater than that achieved with either strain C9-1 or strain A506. In the field test with apple, pathogen suppression by E325 was approximately 35-fold greater than that achieved with strain C9-1 and about 75-fold greater than that achieved with strain A506.

Example 4

The following example describes laboratory tests in which *Erwinia herbicola* strain E325 was compared to 110 other strains of *Erwinia herbicola*.

Materials and Methods.

A total of 109 strains of *Erwinia herbicola*, including E325, were collected by individuals at the USDA-ARS Tree Fruit Research Laboratory, Wenatchee, Wash. These were isolated from 1987 to 1995 and most came from the flowers or fruit of apple or pear. Two additional strains from other researchers and locations, strains C9-1 and Eh252, were tested. Strain C9-1, which was included in Example 3, was originally isolated in Michigan by C. Ishimaru. Strain Eh252 was obtained from S. Beer; he or one of his coworkers collected it in New York. Both C9-1 and Eh252 have been mentioned in the scientific literature as biocontrol agents of fire blight.

A series of small tests, each involving 10 to 20 of the 111 total strains of *Erwinia herbicola*, were conducted in the laboratory with detached flowers as described in Example 2. Based on these results, the best twenty out the 111 total were selected and tested together in two trials. Five flowers were used per strain per test and data from the two tests were pooled.

Results.

Figure 2:
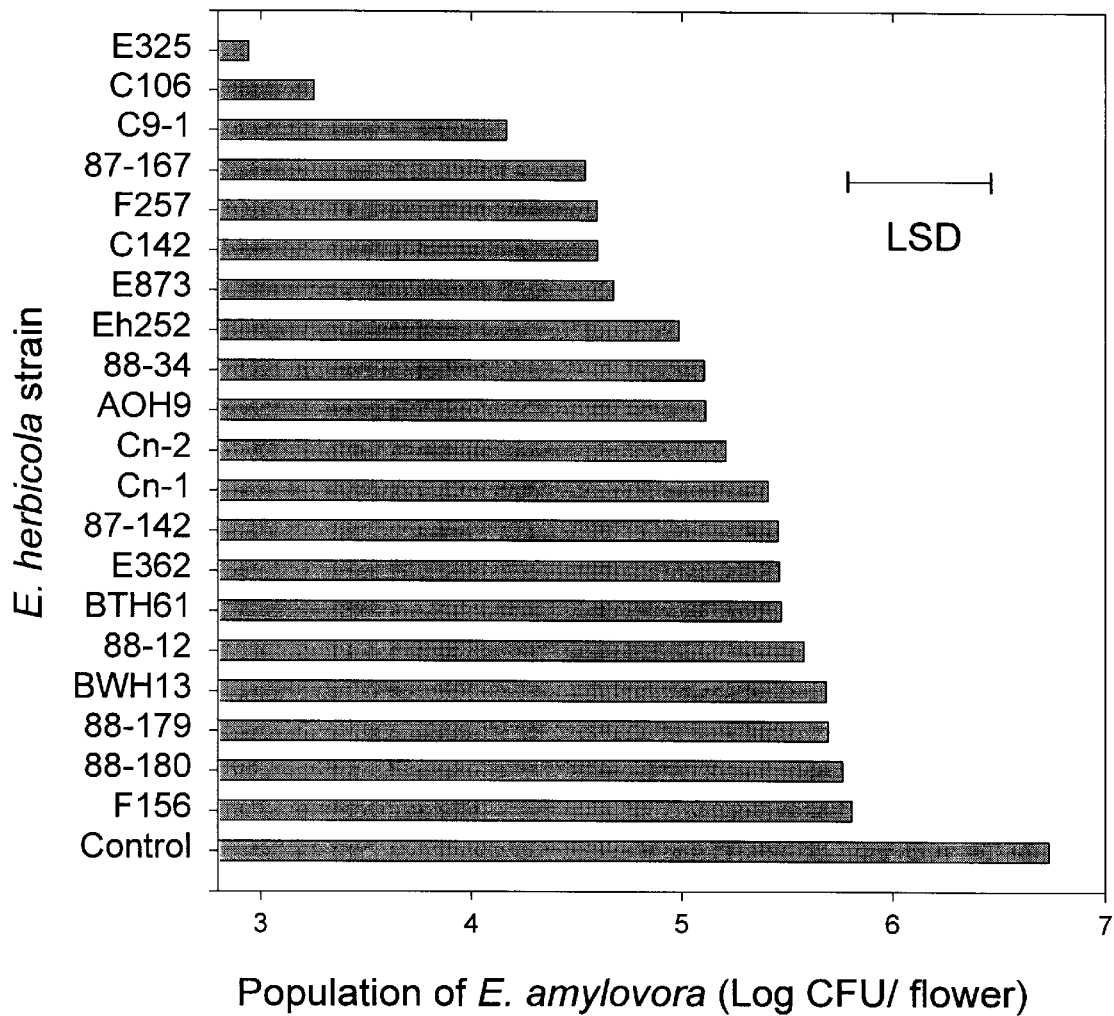
FIG. 2 shows the effects of 20 strains of *Erwinia herbicola,* including the strain of the invention, in suppressing populations of *Erwinia amylovora* on detached crab apple flowers. The strains were selected from among a total of 111 strains of *Erwinia herbicola* based on a series of previous tests. Five flowers were used per strain per each of two tests, and data from the two tests were pooled. Line indicates least significant difference (LSD) at $P \leq 0.05$.

The results are shown in FIG. 2. As can be seen from the figure, population sizes of *Erwinia amylovora* on flower stigmas were more than one log unit (or more than 10 fold) lower than those on flowers treated with any other strain of *Erwinia herbicola,* except strain C106. C106 is a strain isolated by a USDA researcher from pear flowers as part of a study of the microflora on the surfaces of pear flowers. It had been placed in the USDA collection at Wenatchee, Wash. However, no efficacy of C106 for fire blight had been determined or reported prior to this present study.

It is understood that the foregoing detailed description is given merely by way of illustration and that modification and variations may be made within, without departing from the spirit and scope of the invention.

What is claimed is:

1. A biologically pure culture of a strain of *Erwinia herbicola* having all of the identifying characteristics of *Erwinia herbicola* NRRL B-21856, which is effective to inhibit the incidence or severity of fire blight disease on pome fruit trees caused by *Erwinia amylovora.*

2. A composition for controlling fire blight disease on pome fruit trees, which comprises the strain of claim 1 and an agriculturally acceptable carrier.

3. The composition as described in claim 2 wherein said carrier comprises water.

4. The composition as described in claim 2 wherein said strain is present in an amount effective to inhibit the incidence or severity of fire blight disease on pome fruit trees caused by *Erwinia amylovora.*

5. A method of inhibiting the incidence or severity of the disease caused by *Erwinia amylovora* on pome fruit trees, which comprises applying an effective inhibiting amount of the biologically pure culture of claim 1 to the pone fruit trees.

* * * * *